United States Patent [19]

Tennant et al.

[11] Patent Number: 5,399,742
[45] Date of Patent: Mar. 21, 1995

[54] LOW PRESSURE PROCESS FOR THE MANUFACTURE OF CYCLOHEXANEDICARBOXYLATE ESTERS

[75] Inventors: Brent A. Tennant; Mark D. Williams; Bruce L. Gustafson, all of Kingsport, Tenn.

[73] Assignee: Eastman Chemical Company, Kingsport, Tenn.

[21] Appl. No.: 225,871

[22] Filed: Apr. 11, 1994

Related U.S. Application Data

[63] Continuation-in-part of Ser. No. 76,676, Jun. 15, 1993.

[51] Int. Cl.$^6$ ............................................... C07C 69/74
[52] U.S. Cl. ..................................................... 560/127
[58] Field of Search ........................................ 560/127

[56] References Cited

U.S. PATENT DOCUMENTS

| | | | |
|---|---|---|---|
| 2,070,770 | 2/1937 | Amend | 560/127 |
| 2,675,390 | 4/1954 | Rosenblatt | 560/127 |
| 3,205,278 | 9/1965 | Lapporte | 560/127 |
| 3,334,149 | 8/1967 | Akin | 260/617 |

*Primary Examiner*—Michael L. Shippen
*Attorney, Agent, or Firm*—J. Frederick Thomsen; Bernard J. Graves

[57] ABSTRACT

Disclosed is a process for the manufacture of dialkyl cyclohexanedicarboxylates by the low pressure, catalytic hydrogenation of the corresponding dialkyl benzenedicarboxylate wherein the formation/accumulation of carbon monoxide is suppressed to maintain the activity of the precious metal catalyst.

6 Claims, 1 Drawing Sheet

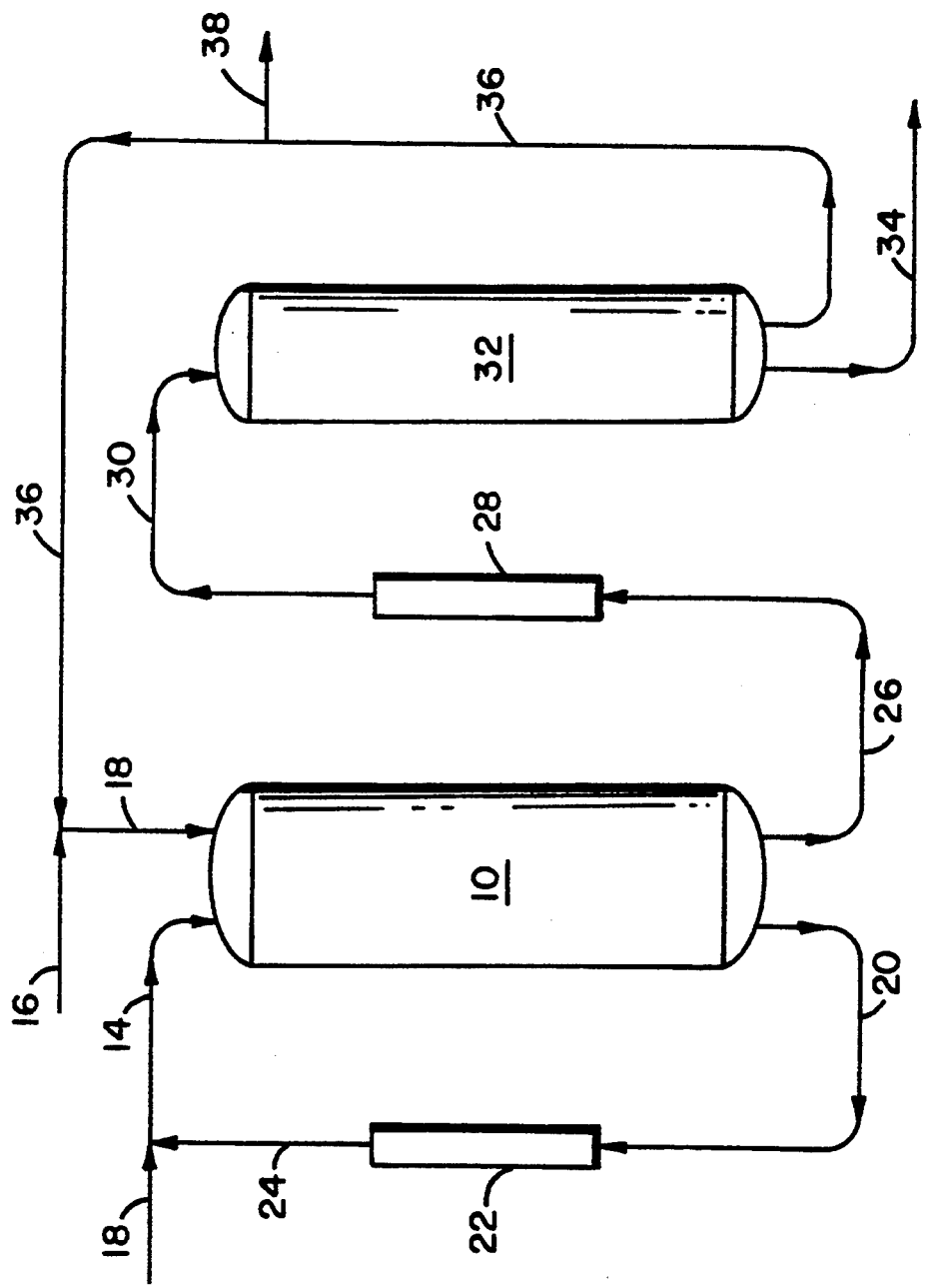

LOW PRESSURE PROCESS FOR THE MANUFACTURE OF CYCLOHEXANEDICARBOXYLATE ESTERS

This application is a continuation-in-part of our application Ser. No. 08/076,676, filed Jun. 15, 1993.

This invention pertains to a process for the manufacture of dialkyl cyclohexanedicarboxylates by the low pressure, catalytic hydrogenation of the corresponding dialkyl benzenedicarboxylate. More particularly, this invention pertains to the low pressure, catalytic hydrogenation of a dialkyl benzenedicarboxylate wherein the formation/accumulation of carbon monoxide is suppressed to maintain the activity of the precious metal catalyst.

Dimethyl 1,4-cyclohexanedicarboxylate has been manufactured on a commercial scale for over 30 years as an intermediate in the production of cyclohexanedimethanol, a diol which is used extensively as a monomer in the preparation of condensation polymers, particularly polyesters. Dimethyl cyclohexanedicarboxylates also are valuable chemical intermediates useful, for example, in the manufacture of polyester resins used in the formulation of coating compositions.

The manufacture of dimethyl 1,4-cyclohexanedicarboxylate and 1,4-cyclohexanedimethanol using dimethyl terephthalate as the feedstock and a heterogenous mode of operation is described in U.S. Pat. No. 3,334,149. This patent describes a continuous process wherein molten dimethyl terephthalate flows over and through a bed of a supported palladium catalyst in a mode of operation referred to as trickle bed operation. The continuous process described requires the use of high pressures, e.g., greater than 346 bars absolute (5018 pounds per square inch absolute—psia), and utilizes a palladium on alumina catalyst in the hydrogenation of dimethyl terephthalate to dimethyl 1,4-cyclohexanedicarboxylate. The specific palladium on alumina employed is in the form of 3 mm chips and contains 0.5 weight percent-palladium deposited on alumina, the crystalline phase of which is a mixture of bayerite and boehmite.

It is apparent that chemical processes which require the use of high pressures such as pressures in excess of 340 bars (4931 psia) are inherently expensive due to the increased operating costs and the cost of the apparatus required including the high pressure-rated reactor and the compressors. However, when the hydrogenation of dimethyl terephthalate to dimethyl 1,4-cyclohexanedicarboxylate is carried out at pressures less than 175 bars absolute (2538 psia) using the above-described palladium on alumina catalyst, commercially acceptable hydrogenation rates cannot be achieved and/or maintained. For example, when operating at 125 bars absolute (1813 psia), the hydrogenation rate typically is significantly less than the rates achieved at approximately 410 bars absolute (5947 psia) pressure. In some cases, the hydrogenation reaction can decrease to a rate of zero. The reduced hydrogenation rate is due to decreased activity of the palladium catalyst which, we have discovered, is related to the generation of carbon monoxide during the hydrogenation at lower pressures. It has been found that the hydrogenation of dimethyl benzenedicarboxylates at relatively low pressures, e.g., pressures of less than about 175 bars absolute (2538 psia), results in the formation of carbon monoxide, possibly by the decomposition of the methanol liberated from the dimethyl ester. The problem of carbon monoxide formation and/or catalyst deactivation is not encountered when the hydrogenation is carried out at the high pressures described in U.S. Pat. No. 3,334,149. It is known that the presence of carbon monoxide in hydrogen gas used in catalytic hydrogenation processes is detrimental to such processes. However, the production of carbon monoxide and the extreme sensitivity of the above-described palladium on alumina catalyst to parts per million (ppm) amounts of carbon monoxide is surprising.

The present invention is concerned with a process whereby a dimethyl benzenedicarboxylate is catalytically hydrogenated to the corresponding dimethyl cyclohexanedicarboxylate using moderate pressures and readily available catalysts. The present invention provides a continuous process for the manufacture of a dimethyl cyclohexanedicarboxylate which comprises the steps of;

(1) continuously feeding hydrogen gas and a liquid mixture of the dimethyl cyclohexanedicarboxylate product and the corresponding dimethyl benzenedicarboxylate reactant to a hydrogenation zone containing at least one fixed bed of a palladium on alumina hydrogenation catalyst; and (2) continuously removing hydrogen gas and a liquid product comprising dimethyl cyclohexanedicarboxylate product from the hydrogenation zone;

wherein the dimethyl benzenedicarboxylate is hydrogenated to the dimethyl cyclohexanedicarboxylate at a pressure of about 10 to 175 bars absolute (14.5 to 2538psia) and a temperature of about 150° to 230° C. and the concentration of carbon monoxide in the hydrogen gas removed from the hydrogenation zone is maintained at less than 100 parts per million by volume (ppmv). Our novel process may be used to produce dimethyl cyclohexanedicarboxylate esters at a conversion of 99% or greater and space-time yields (based on the volume of catalyst) of 1000 g per liter-hour or greater.

Various process conditions and/or modes of operation may be controlled or modified to maintain the carbon monoxide concentration at levels which do not retard significantly the hydrogenation rate of the process. Thus, the concentration of carbon monoxide may be maintained at low levels simply by venting all of the gaseous effluent from the process and feeding only fresh hydrogen which is essentially free of carbon monoxide. However, this mode of operation is economically feasible only if the off-gas consisting primarily of hydrogen and a small amount, e.g., 100 ppmv, of carbon monoxide can be transferred to and used in another chemical process or if the off-gas can be purified to remove the carbon monoxide. Since purging all, or substantially all, of the hydrogen from the hydrogenation process frequently is not practical, the amount of gas which may be purged from the system to control carbon monoxide levels normally is up to about 10 volume percent of the amount of fresh hydrogen fed to the hydrogenation process.

Carbon monoxide formation can be suppressed by operating in a mode which provides a large amount of hydrogen to the catalyst surface. The mass transfer of hydrogen to the catalyst sites must be high enough to avoid having a lower dissolved hydrogen concentration than desired. A recycle stream of hydrogen may be used to increase the gas velocity through the catalyst bed to decrease the liquid hold-up in the reactor which decreases the liquid around the catalyst through which the hydrogen must diffuse. The gas hourly space velocity (GHSV), measured at or under operating conditions, for the hydrogen normally should be at least 2 and preferably in the range of about 3 to 10. The particular hydrogen GHSV which will give satisfactory or optimal results can depend on other process parameters such as the feed rate of the liquid phase comprising the dimethyl cyclohexanedicarboxylate product and dimethyl benzenedicarboxylate reactant to the hydrogenation zone and the temperatures and pressures employed and on the characteristics of the catalyst.

The rate of the exothermic hydrogenation process of the present invention is moderated by feeding the dimethyl benzenedicarboxylate reactant with the dimethyl cyclohexanedicarboxylate product as an inert diluent. The weight ratio of the dimethyl benzenedicarboxylate to the dimethyl cyclohexanedicarboxylate may be in the range of about 1:50 to 1:5 although weight ratios of about 1:20 to 1:10 are preferred. The dimethyl cyclohexanedicarboxylate inert diluent may be provided in the form of a recycle stream of the product effluent. This recycle stream may be passed through a heat exchanger to increase or, more commonly, decrease the temperature of the stream to control the temperature of the hydrogenation zone. In commercial operation, about 80 to 95 weight percent of the product effluent may be recycled to the hydrogenation zone after being combined with fresh dimethyl benzenedicarboxylate reactant.

The dimethyl benzenedicarboxylate reactant must be fed to the hydrogenation zone at a rate which will result in substantially complete conversion of the reactant to the cyclohexanedicarboxylate product. Incomplete conversion of the reactant may cause the formation of hot spots within the catalyst bed and/or runaway reactions. The liquid hourly space velocity (LHSV) of the dimethyl benzenedicarboxylate reactant feed to the hydrogenation zone typically is about 0.3 to 5 and preferably about 0.5 to 2. The most suitable LHSV for the reactant feed is dependent upon the particular temperature and pressure used which, as mentioned hereinabove, can depend upon the flow rate and/or purity of the hydrogen.

The hydrogenation process of the present invention may be carried out over a temperature range of about 150° to 230° C. Generally, higher temperatures favor carbon monoxide formation and therefore the use of temperatures in the upper part of the range require means for removing carbon monoxide from the hydrogenation zone, e.g., by purging all, or substantially all, of the hydrogen effluent of the process. We have demonstrated, for example, that when all other operating conditions are kept constant, decreasing the feed temperature to the primary hydrogenation reactor from 183° C. to 174° C. results in a decrease in (i) the DMT content of the product stream from conduit 34 of the accompanying Figure and (ii) the carbon monoxide concentration in the hydrogen purge gas. When the off-gas purged from the process is 30 volume percent or less of the amount of fresh hydrogen fed, the process preferably is operated within a temperature range of about 160° to 200° C.

The hydrogenation process may be performed within a pressure range of about 10 to 175 bars absolute (14.5 to 2538 psia). At pressures below this range, the hydrogenation rate is low resulting in an unacceptable production rate whereas at pressures above 175 bars absolute, the benefits and advantages provided by our invention are much less significant. The hydrogenation preferably is carried out at a pressure in the range of about 40 to 140 bars absolute (580 to 2031 psia). Our improved process may be used to manufacture 1,2-1,3- and 1,4-cyclohexanedicarboxylate ester by the hydrogenation of the corresponding benzenedicarboxylate ester isomers. The 1,3- and, especially, the 1,4-isomers are the most important products of the process.

The precious metal catalysts useful in our novel process comprise supported palladium catalysts, especially palladium on alumina catalysts wherein palladium comprises about 0.1 to 5.0 weight percent of the catalyst. The preferred palladium on alumina catalysts have the following characteristics:

(1) palladium comprises about 0.5 to 2.0 weight percent of the catalyst;
(2) the palladium dispersion is at least 20 percent;
(3) at least 90 weight percent of the palladium is located on the alumina at a depth less than 200 microns from the surface of the alumina; and
(4) the crystalline phase of the alumina is alpha, theta, delta, eta or a mixture thereof.

The nitrogen BET surface area of the palladium on alumina catalysts used in the process of our invention is in the range of about 20 to 300 square meters per gram ($m^2/g$) with the range of about 30 to 150 $m^2/g$ being preferred. It is well known in the art that BET surface area is a function of crystalline phases and calcination history and should be as high as possible while maintaining the appropriate oxide phase. Catalysts having the characteristics described hereinabove may be prepared according to conventional impregnation or deposition techniques using procedures well known to those skilled in the art. The catalyst may be used in the hydrogenation process in the form of pellets, spheres, extrudates and the like. The particular form is not critical so long as the catalyst form does not lead to excessive channeling of the liquid feed through the reactor, e.g., in continuous operation using a fixed bed of catalyst through which the reactant is passed. Preferably, the surface area:volume ratio of the catalyst is at least 500 and preferably greater than 1500.

BRIEF DESCRIPTION OF DRAWINGS

The accompanying FIGURE is a process flow diagram illustrating the principles of the process of the present invention. Those skilled in the art will recognize that the hydrogenation process may be operated by modifying the particular equipment depicted in the FIGURE.

Referring to the FIGURE, reactor 10 is fed with a liquid mixture of dimethyl benzenedicarboxylate reactant and dimethyl cyclohexanedicarboxylate diluent by means of conduits 12 and 14 and hydrogen is supplied to reactor 10 by conduits 16 and 18. Reactor 10 constitutes the primary hydrogenation zone of the process system depicted in the FIGURE and may be a generally columnar pressure vessel containing one or more fixed beds of a palladium on alumina hydrogenation catalyst. A portion of the liquid product and hydrogen gas is removed from the base of vessel 10 by conduit 20, passed through heat exchanger 22 and recycled by means of conduits 24 and 14 to the top or upper portion of reactor 10. Heat exchanger 22 is used to increase or, more typically, to decrease the temperature of the recycle stream and thus aid in the control of the temperature within the primary hydrogenation reactor including the temperature gradient over the length of the catalyst bed or beds contained therein.

The recycle stream of conduits 20, 24 and 14 provides all of the cyclohexanedicarboxylate diluent which is combined with dimethyl benzenedicarboxylate reactant fed via conduit 12 and fed to reactor 10. The recycle liquid typically constitutes about 80 to 90 weight percent of the total liquid effluent of reactor 10. The degree of conversion of the dimethyl benzenedicarboxylate reactant fed to reactor 10 usually is about 92 to 99 mole percent, preferably about 95 to 98 mole percent.

A second portion of the liquid product and hydrogen gas is removed from the base of vessel 10 by conduit 26, passed through heat exchanger 28 and fed by conduit 30 to the top or upper portion of reactor 32 wherein the overall conversion of the dimethyl benzenedicarboxylate reactant fed to hydrogenation process is increased to at least 99.9 mole percent. Reactor 32 constitutes the secondary hydrogenation zone of the process system depicted in the FIGURE and may be a generally columnar, pressure vessel containing one or more fixed beds of a palladium on alumina hydrogenation catalyst. Dimethyl cyclohexanedicarboxylate product is removed from reactor 32 by means of conduit 34. The product normally has a purity of at least 99 mole percent.

The hydrogen gas effluent of reactor 32 is recycled by conduits 36 and 18 to reactor 10. Approximately 30 to 100 volume percent of this gas recycle stream is purged from the process through conduit 38 to aid in the maintenance of the carbon monoxide in the stream to less than 100 ppmv. To suppress the formation/accumulation of carbon monoxide within the catalyst beds, the gas hourly space velocity of the hydrogen gas is in the range of about 2 to 10 measured under operating conditions. The volume ratio of recycle hydrogen supplied via conduit 36 to fresh hydrogen supplied via conduit 16 usually is in the range of about 0.1:1 to 1:1.

In a preferred embodiment of the present invention, the hydrogenation process is carried out using at least 2 hydrogenation zones: a primary zone and a secondary zone comprising a total of two or more reactors. A mixture of fresh dimethyl benzenedicarboxylate reactant and dimethyl cyclohexanedicarboxylate diluent is fed to the primary hydrogenation zone along with a mixture of fresh and recycled hydrogen. About 92 to 99, preferably 95 to 98, mole percent of the dimethyl benzenedicarboxylate reactant is converted to dimethyl cyclohexanedicarboxylate product in the primary hydrogenation zone. Approximately 80 to 95 weight percent of the liquid effluent exiting the primary hydrogenation zone is recycled and fed to the primary zone along with the fresh dimethyl benzenedicarboxylate reactant.

The remainder of the liquid effluent (the portion not recycled) and the off-gas from the primary hydrogenation zone is fed to the secondary hydrogenation zone wherein the overall conversion of the dimethyl benzenedicarboxylate reactant to dimethyl cyclohexanedicarboxylate product is increased to at least 99.0, preferably at least 99.9, mole percent. The vapor effluent comprising hydrogen from the secondary hydrogenation zone is recycled and fed to the primary hydrogenation zone. Normally, a portion, e.g., about 5 to 30 volume percent, of this recycle stream is purged from the hydrogenation system to maintain the carbon monoxide concentration in the recycle fed to the primary zone to less than about 100 ppmv.

The above-described preferred embodiment of our invention therefore concerns a process for the manufacture of a dimethyl cyclohexanedicarboxylate which comprises the steps of:

I. continuously feeding hydrogen gas and a liquid mixture of the dimethyl cyclohexanedicarboxylate product and the corresponding dimethyl benzenedicarboxylate reactant to a primary hydrogenation zone containing at least one fixed bed of a palladium on alumina hydrogenation catalyst wherein the dimethyl benzenedicarboxylate is hydrogenated to the dimethyl cyclohexanedicarboxylate;

II. continuously removing hydrogen gas and a liquid product comprising dimethyl cyclohexanedicarboxylate product and unreacted dimethyl benzenedicarboxylate from the primary hydrogenation zone;

III. continuously recycling about 80 to 95 weight percent of the liquid product from II to the primary hydrogenation zone;

IV. continuously feeding the liquid product which is not recycled and the hydrogen gas from II to a secondary hydrogenation zone wherein unreacted dimethyl benzenedicarboxylate is hydrogenated to the dimethyl cyclohexanedicarboxylate;

V. continuously removing hydrogen gas and a liquid product comprising dimethyl cyclohexanedicarboxylate product at a dimethyl benzenedicarboxylate conversion rate of at least 99 mole percent from the secondary hydrogenation zone;

VI. purging from 5 to 30 volume percent of the hydrogen gas from V from the hydrogenation process; and VII. recycling the hydrogen gas from V which is not purged from the process to the primary hydrogenation zone;

wherein the hydrogenation is carried out at a pressure of about 10 to 175 bars absolute (14.5 to 2538 psia) and a temperature of about 150° to 230° C. and the concentration of carbon monoxide in the hydrogen gas removed from the hydrogenation zone is maintained at less than 100 parts per million by volume (ppmv).

The process provided by our invention is further illustrated by the following examples. Examples 1–3, wherein amounts of materials are specified in parts by weight except for the amount of hydrogen which is specified in parts by volume, were carried out using the process system depicted in the FIGURE. Primary hydrogenation reactor 10 contained 12 parts of a hydrogenation catalyst comprising 0.5% palladium on alumina and secondary hydrogenation reactor 32 contained 6 parts of the same hydrogenation catalyst.

EXAMPLE 1

A mixture of 10 weight percent dimethyl 1,4-benzenedicarboxylate (dimethyl terephthalate, DMT) and 90 weight percent dimethyl 1,4-cyclohexanedicarboxylate (DMCD) was fed to reactor 10 at a rate of 96 parts per hour and a temperature of 186° C. Hydrogen gas comprising approximately 33 volume percent fresh hydrogen supplied by conduit 12 and approximately 67 volume percent supplied by conduit 36 was fed to reactor 10 through conduit 14 at a rate of 0.9 parts per hour. The hydrogen feed rate represented a GHSV of about 6.8 based on the volume of catalyst in both reactors 10 and 32. About 90 weight percent of the liquid effluent of reactor 10 was recycled by conduits 20, 24 and 14. The pressure within reactors 10 and 32 was maintained at approximately 124 bars absolute (1799 psia)±1 bar.

The reactor 10 liquid and gas effluents not recycled were transported by conduit 26, heat exchanger 28 and conduit 30 and fed to secondary hydrogenation reactor 32 at a temperature of 194° C. DMCD containing less than about 0.2 weight percent DMT was removed from reactor 32 by conduit 34 at a rate of 9.9 parts per hour. The hydrogen gas effluent of reactor 32 was recycled by conduits 36 and 18 to primary hydrogenation reactor 10. Hydrogen gas was purged from the process by conduit 38 at a rate of 0.03 parts per hour.

While the process system was operated at the production rates described above, the system was stable as evidenced by the fact that the temperature of the liquid fed and the liquid removed from reactor 10 remained substantially the same. When the feed of DMT to reactor 10 was increased to 10.9 parts per hour, the temperature of the liquid removed from reactor 10 decreased, rather than increased, and continued to decrease with time, showing a decrease in reaction rate within reactor 10. This decreased reaction rate was further established by an increase in the amount of DMT in the product and an increase of 13 weight percent of the DMT in the recycle stream of conduit 20. Upon reducing the DMT feed rate to 8.6 parts per hour, the system returned to normal as evidence by the DMT content of the recycle liquid and product.

EXAMPLE 2

The process was operated as described in Example 1 except that (i) the DMT feed rate to reactor 10 was 10.9 parts per hour and (ii) the hydrogen purge rate via conduit 38 was 0.3 parts per hour. Thus, hydrogen comprising 50 volume percent fresh hydrogen and 50 volume percent recycle hydrogen was fed to reactor 10 through conduit 18 at a rate of 1.2 parts per hour. The use of these process parameters resulted in smooth, steady state operation of the process. The increase in the amount of the hydrogen gas purge permitted an increase in the rate of DMT addition without a decrease in reaction rate caused by the formation/accumulation of carbon monoxide in the catalyst bed.

The hydrogen purge rate then was decreased to approximately 0.15 parts per hour. The carbon monoxide concentration in the gas purged through conduit 38 increased from 74 ppmv to over 100 ppmv, showing that carbon monoxide is not in equilibrium and that higher purge rates reduce the concentration of carbon monoxide which provides more stable operation.

EXAMPLE 3

The process was operated as described in Example 1 except that (i) the DMT feed rate to reactor 10 was 10.9 parts per hour and (ii) the hydrogen purge rate via conduit 38 was 0.3 parts per hour. Thus, hydrogen comprising 100 volume percent fresh hydrogen and 0 volume percent recycle hydrogen was fed to reactor 10 through conduit 18 at a rate of about 0.6 parts per hour. The DMT content of the material transported by lines 20 and 26 was 6.5 weight percent. The velocity of the hydrogen gas within conduit 18 was increased resulting in an increase of the hydrogen feed rate to reactor 10 to 1.2 parts per hour. The DMT content of the liquid on lines 20 and 26 decreased to 2.9 weight percent and the carbon monoxide content of the hydrogen gas purged via conduit 38 decreased from greater than 100 ppmv to 58 ppmv. This process modification demonstrates the advantages provided by increasing the flow rate of the hydrogen gas.

EXAMPLES 4-8

Experiments 4-8 were performed in a trickle bed reactor system which comprised a 1.83 meter (6 feet) section of 316 stainless steel pipe having an interior diameter of 2.5 cm (1 inch) and equipped with means for liquid recycle. The catalyst (800 cc) was held in place within the reactor by 100 cc of 1.6 mm (0.0625 inch) 316 stainless steel Penn State packing located above and below the catalyst bed. The temperatures at various points within the catalyst bed were measured by 10 thermocouples which extended through the reactor wall and approximately 3.2 mm into the catalyst. The temperature reported in each example is the average of these readings. Typical temperature gradients through the bed were less than 10° C. The catalyst employed in Examples 4-8 was a 0.5% palladium on alumina chipped catalyst identical to the palladium catalyst used by Akin et al in the examples of U.S. Pat. No. 3,334,149.

The catalyst was activated by heating the system under nitrogen to 150° C. while flowing dimethyl 1,4-cyclohexanedicarboxylate (DMCD) through the reactor system at 5 Kg per hour at 70 bars absolute (1030 psia) pressure with a 10 Kg per hour liquid recycle. The feed gas then was switched to hydrogen (99.999 %) and the pressure slowly increased to 125 bars (1815 psia) and, finally, the temperature was raised to the desired reaction temperature. The hydrogenation reaction was commenced by switching the reactor feed from DMCD to a 30:70 weight:weight mixture of dimethyl terephthalate and DMCD (also fed at a rate of 5 Kg per hour). Hydrogen was purged from the system at a rate of 8 to 10 normal L per minute. Carbon monoxide concentrations in the purged hydrogen gas were measured using a Beckman IR carbon monoxide analyzer. Operating data were recorded when steady state of operation was achieved, typically 1 to 2 hours from commencement of the reaction.

Dimethyl terephthalate was hydrogenated at a temperature of 180° C. and at pressures of 70, 104.4, 125, 173.3, and 207.8 bars absolute (1015, 1515, 1815, 2515, and 3015 psia). Each of the examples was carried out at one of the pressures specified for a period of 1 to 2 hours and, as stated above, operating data were recorded when steady state of operation was achieved. The ester product obtained in each example was analyzed and the rate of hydrogenation or conversion (g per hour) of dimethyl terephthalate was determined. Also, the concentration of carbon monoxide was determined as described above during steady operation at each of the pressures specified.

The results obtained in Examples 4-8 are set forth in Table I wherein "CO" is the concentration (in parts per million, ppm) of carbon monoxide in the purge gas and "Rate" is the rate (in g per hour) of the hydrogenation of dimethyl terephthalate.

TABLE I

| | Example | | | | |
|---|---|---|---|---|---|
| | 4<br>90 Bars | 5<br>104.4 Bars | 6<br>125 Bars | 7<br>173.3 Bars | 8<br>207.8 Bars |
| CO | 74 | 47 | 28 | 15 | 9 |
| Rate | 938 | 1259 | 1411 | 1452 | 1455 |

It is apparent from the data presented in Table I that in the reaction system wherein dimethyl terephthalate is hydrogenated to dimethyl cyclohexanedicarboxylate at 180° C.:

(i) below 175 bars, the formation and accumulation of CO is inversely proportional to the pressure within the reaction system;

(ii) the rate at which dimethyl terephthalate is hydrogenated to dimethyl cyclohexanedicarboxylate decreases as (a) the pressure within the reaction system decreases and (b) the concentration of CO in the reactor purge gas increases; and (iii) the concentration of CO in the reactor purge gas is very low (9 ppm) when dimethyl terephthalate is hydrogenated to dimethyl cyclohexanedicarboxylate at a pressure above 175 bars, e.g., about 207.8 bars.

EXAMPLE 9–11

Dimethyl terephthalate was hydrogenated at a temperature of 200° C. and a pressure of 125 bars absolute (1815 psia) according to the procedure described in Examples 4–8 except that hydrogen was purged from the system at a rate of 3.1 Normal liters per minute and the liquid recycle was 10 Kg per hour. Each of Examples 9, 10 and 11 was of 1 to 2 hours duration and, as stated above, operating data were recorded when steady state of operation was achieved. The ester product obtained in each example was analyzed and the rate of hydrogenation (g per hour) of dimethyl terephthalate was determined. In Example 9, the hydrogen gas fed to the reactor system was essentially pure whereas in Examples 10 and 11 the hydrogen gas contained 35 ppm and 70 ppm carbon monoxide, respectively. The results obtained in Examples 9–11 are set forth in Table II wherein "CO" and "Rate" are defined above.

TABLE II

| | Example | | |
|---|---|---|---|
| | 9 | 10 | 11 |
| CO | 0 | 35 | 70 |
| Rate | 1411 | 1319 | 1294 |

The data presented in Table II establishes that under substantially identical conditions, the presence of 35 and 70 ppm carbon monoxide in the hydrogen gas fed to the hydrogenation system suppresses significantly the rate of production of dimethyl 1,4-cyclohexanedicarboxylate from dimethyl terephthalate. Furthermore, the results obtained in Example 11 were erratic and thus, the hydrogenation process at 200° C. and 125 bars is unstable in the presence of 70 ppm carbon monoxide.

EXAMPLES 12–16

Dimethyl terephthalate was hydrogenated at a temperature of 181°–184° C. and a pressure of 125 bars absolute (1815 psia) using a hydrogen purge of 9–10 Normal L per minute according to the procedure described in Examples 9–11 except that the catalyst was 1% palladium on alumina pellets supplied by Englehard Industries. Examples 12–16 were carried out in sequential order to demonstrate that the detrimental effect of carbon monoxide is reversible. The ester product obtained in each example was analyzed and the rate of hydrogenation (g per hour) of dimethyl terephthalate was determined. In Examples 12, 14 and 16, the hydrogen gas fed to the reactor system was essentially pure whereas in Examples 13 and 15 the hydrogen gas contained 57 ppm and 37 ppm carbon monoxide, respectively. The results obtained in Examples 12–16 are set forth in Table III wherein "CO" and "Rate" are defined above, "Temp" is the temperature (0° C.) measured as described in Examples 4–8, "DMT Feed Rate" is the rate in g per hour at which dimethyl terephthalate was fed to the trickle bed reactor, and "% DMT Prod" is the weight per cent dimethyl terephthalate present in the ester product obtained from the reactor.

TABLE III

| Example | CO | DMT Feed Rate | % DMT Prod | Rate |
|---|---|---|---|---|
| 12 | 0 | 1553 | 2.6 | 1418 |
| 13 | 57 | 1462 | 9.0 | 1023 |
| 14 | 0 | 1584 | 2.1 | 1473 |
| 15 | 37 | 1550 | 4.8 | 1302 |
| 16 | 0 | 1492 | 1.9 | 1398 |

The results reported in Table III further illustrate the adverse effects carbon monoxide has on the activity of a supported palladium catalyst. More specifically, such adverse effect on catalyst activity are established for Examples 13 and 15 by (1) the lower rate of hydrogenation of dimethyl terephthalate and (2) the higher concentrations of unconverted (unreacted) dimethyl terephthalate in the product.

The invention has been described in detail with particular reference to preferred embodiments thereof, but it will be understood that variations and modifications can be effected within the spirit and scope of the invention.

We claim:

1. Continuous process for the manufacture of a dimethyl cyclohexanedicarboxylate which comprises the steps of:
   (1) continuously feeding hydrogen gas and a liquid mixture of the dimethyl cyclohexanedicarboxylate product and the corresponding dimethyl benzenedicarboxylate reactant to a hydrogenation zone containing at least one fixed bed of a palladium on alumina hydrogenation catalyst; and
   (2) continuously removing hydrogen gas and a liquid product comprising dimethyl cyclohexanedicarboxylate product from the hydrogenation zone;

wherein the dimethyl benzenedicarboxylate is hydrogenated to the dimethyl cyclohexanedicarboxylate at a pressure of about 10 to 175 bars absolute and a temperature of about 150° to 230° C. and the concentration of carbon monoxide in the hydrogen gas removed from the hydrogenation zone is maintained at less than 100 parts per million by volume (ppmv).

2. Process according to claim 1 wherein the gas hourly space velocity of the hydrogen through the hydrogenation zone is at least 2.

3. Process according to claim 1 wherein the gas hourly space velocity of the hydrogen through the hydrogenation zone is at least 2 and the weight ratio of the dimethyl benzenedicarboxylate to the dimethyl cyclohexanedicarboxylate is in the range of about 1:20 to 1:10.

4. Continuous process for the manufacture of a dimethyl cyclohexanedicarboxylate which comprises the steps of:
   (1) continuously feeding hydrogen gas and a liquid mixture of the dimethyl cyclohexanedicarboxylate product and the corresponding dimethyl benzenedicarboxylate reactant to a hydrogenation zone containing at least one fixed bed of a palladium on alumina hydrogenation catalyst; and (2) continuously removing hydrogen gas and a liquid product comprising dimethyl cyclohexanedicarboxylate product from the hydrogenation zone;

wherein the dimethyl benzenedicarboxylate is hydrogenated at a conversion rate of at least 99 mole percent to the dimethyl cyclohexanedicarboxylate at a pressure of about 40 to 140 bars absolute and a temperature of about 160° to 200° C., the concentration of carbon monoxide in the hydrogen gas removed from the hydrogenation zone is maintained at less than 100 parts per million by volume, the gas hourly space velocity of the hydrogen through the hydrogenation zone is about 3 to 10, the weight ratio of the dimethyl benzenedicarboxylate to the dimethyl cyclohexanedicarboxylate is in the range of about 1:20 to 1:10 and the liquid hourly space velocity of the dimethyl benzenedicarboxylate is about 0.3 to 5.

5. Process for the manufacture of a dimethyl cyclohexanedicarboxylate which comprises the steps of:
I. continuously feeding hydrogen gas and a liquid mixture of the dimethyl cyclohexanedicarboxylate product and the corresponding dimethyl benzenedicarboxylate reactant to a primary hydrogenation zone containing at least one fixed bed of a palladium on alumina hydrogenation catalyst wherein the dimethyl benzenedicarboxylate is hydrogenated to the dimethyl cyclohexanedicarboxylate;
II. continuously removing hydrogen gas and a liquid product comprising dimethyl cyclohexanedicarboxylate product and unreacted dimethyl benzenedicarboxylate from the primary hydrogenation zone;
III. continuously recycling about 80 to 95 weight percent of the liquid product from II to the primary hydrogenation zone;
IV. continuously feeding the liquid product which is not recycled and the hydrogen gas from II to a secondary hydrogenation zone wherein unreacted dimethyl benzenedicarboxylate is hydrogenated to he dimethyl cyclohexanedicarboxylate;
V. continuously removing hydrogen gas and a liquid product comprising dimethyl cyclohexanedicarboxylate product having a purity of at least 99 mole percent from the secondary hydrogenation zone;
VI. purging from 5 to 30 volume percent of the hydrogen gas from V from the hydrogenation process; and
VII. recycling the hydrogen gas from V which is not purged from the process to the primary hydrogenation zone;

wherein the hydrogenation is carried out at a pressure of about 10 to 175 bars absolute and a temperature of about 150° to 230° C. and the concentration of carbon monoxide in the hydrogen gas removed from the hydrogenation zone is maintained at less than 100 parts per million by volume (ppmv).

6. Process according to claim 5 wherein the hydrogenation is carried out at a pressure of about 40 to 140 bars absolute and a temperature of about 160° to 200° C.

* * * * *

UNITED STATES PATENT AND TRADEMARK OFFICE
CERTIFICATE OF CORRECTION

PATENT NO. : 5,399,742

DATED : March 21, 1995

INVENTOR(S) : Brent A. Tennant et al.

It is certified that error appears in the above-identified patent and that said Letters Patent is hereby corrected as shown below:

In the Figure on page 2, please delete the first listed "18" at the top left margin and insert therefor ---12---.

Column 6, line 63, please delete "conduit 12" and insert therefor ---conduit 16---.

line 65, please delete "conduit 14" and insert therefor ---conduit 18---.

Signed and Sealed this

Nineteenth Day of May, 1998

Attest:

BRUCE LEHMAN

Attesting Officer

Commissioner of Patents and Trademarks